US007749169B2

(12) United States Patent
Bayer et al.

(10) Patent No.: US 7,749,169 B2
(45) Date of Patent: Jul. 6, 2010

(54) HANDHELD BREATH TESTER HOUSING AND MOUTHPIECE

(75) Inventors: David J. Bayer, Richmond Heights, MO (US); M. Rankine Forrester, St. Louis, MO (US); Joe E. Fodor, Sr., Fenton, MO (US)

(73) Assignees: Intoximeters, Inc., St. Louis, MO (US); Alcotek, Inc., St. Louis, MO (US)

( * ) Notice: Subject to any disclaimer, the term of this patent is extended or adjusted under 35 U.S.C. 154(b) by 946 days.

(21) Appl. No.: 10/820,492

(22) Filed: Apr. 8, 2004

(65) Prior Publication Data

US 2004/0260194 A1 Dec. 23, 2004

Related U.S. Application Data

(60) Provisional application No. 60/462,122, filed on Apr. 10, 2003, provisional application No. 60/525,423, filed on Nov. 26, 2003.

(51) Int. Cl.
*A61B 5/08* (2006.01)
*G01N 1/22* (2006.01)
*G01N 31/00* (2006.01)

(52) U.S. Cl. ........................ 600/532; 73/23.3; 422/84

(58) Field of Classification Search ......... 600/529–543, 600/397, 300; 436/132; 422/98, 184, 102, 422/83, 84; 128/107.14, 719, 730, 200.24, 128/204.25, 205.23, 204.22; 73/23.3, 863.01, 73/864.62, 863.11
See application file for complete search history.

(56) References Cited

U.S. PATENT DOCUMENTS

| | | | | | |
|---|---|---|---|---|---|
| 659,962 | A | * | 10/1900 | Goodrich | ................... 29/57 |
| 3,877,291 | A | * | 4/1975 | Hoppesch et al. | ............ 73/23.3 |
| 3,880,591 | A | * | 4/1975 | Burroughs | ................... 600/529 |
| 4,122,842 | A | * | 10/1978 | Pikul | ........................... 600/538 |
| 4,202,353 | A | * | 5/1980 | Hirsch et al. | ................. 600/537 |
| 4,233,842 | A | * | 11/1980 | Raemer et al. | ........... 73/861.04 |
| 4,274,425 | A | * | 6/1981 | Lutz et al. | .................... 600/532 |
| 4,292,978 | A | * | 10/1981 | Guth | ........................... 600/543 |
| 4,649,027 | A | * | 3/1987 | Talbot | ........................... 422/84 |

(Continued)

FOREIGN PATENT DOCUMENTS

WO 0126021 A1 4/2001

(Continued)

OTHER PUBLICATIONS

European Patent Office Search Report, PCT/US2004-024298, Mar. 5, 2008.

*Primary Examiner*—Charles A Marmor, II
*Assistant Examiner*—Navin Natnithithadha
(74) *Attorney, Agent, or Firm*—Armstrong Teasdale LLP

(57) ABSTRACT

A breath tester housing assembly is provided. The assembly comprises a housing having a base to be gripped by an operator, a display oriented to be in line with an operator's direct line of view while gripping the base, and a mouthpiece interface for interfacing with a removable mouthpiece so that when a subject blows into the mouthpiece, the display is not in the direct line of view of the subject. The assembly further comprises a mouthpiece for engaging to the mouthpiece interface. The mouthpiece comprises a body having a substantially planar surface.

32 Claims, 9 Drawing Sheets

U.S. PATENT DOCUMENTS

| | | | | |
|---|---|---|---|---|
| 4,656,008 | A * | 4/1987 | Gump | 422/86 |
| 4,744,953 | A * | 5/1988 | Wolf et al. | 422/84 |
| 4,749,553 | A * | 6/1988 | Lopez et al. | 422/84 |
| 4,900,514 | A * | 2/1990 | Fuller | 600/397 |
| 4,902,628 | A * | 2/1990 | Blair | 436/132 |
| 4,914,038 | A * | 4/1990 | Jewitt | 436/132 |
| 4,996,161 | A * | 2/1991 | Conners et al. | 436/132 |
| 5,027,809 | A * | 7/1991 | Robinson | 128/203.24 |
| 5,060,655 | A * | 10/1991 | Rudolph | 600/529 |
| 5,137,026 | A * | 8/1992 | Waterson et al. | 600/538 |
| 5,291,898 | A * | 3/1994 | Wolf | 600/532 |
| 5,303,575 | A * | 4/1994 | Brown et al. | 73/23.3 |
| 5,337,739 | A * | 8/1994 | Lehman | 128/205.27 |
| 5,445,160 | A * | 8/1995 | Culver et al. | 600/532 |
| 5,735,287 | A | 4/1998 | Thomson | |
| 5,802,909 | A * | 9/1998 | Faulder et al. | 73/23.3 |
| 5,836,300 | A * | 11/1998 | Mault | 128/204.23 |
| 5,924,994 | A * | 7/1999 | Harbrecht et al. | 600/532 |
| 5,957,127 | A * | 9/1999 | Yamamori et al. | 128/204.22 |
| 6,019,731 | A * | 2/2000 | Harbrecht et al. | 600/532 |
| 6,026,674 | A * | 2/2000 | Gammenthaler | 73/19.01 |
| 6,044,843 | A * | 4/2000 | O'Neil et al. | 128/204.23 |
| 6,150,177 | A * | 11/2000 | Stock | 436/132 |
| 6,190,326 | B1 * | 2/2001 | McKinnon et al. | 600/529 |
| 6,190,327 | B1 * | 2/2001 | Isaacson et al. | 600/529 |
| 6,273,087 | B1 * | 8/2001 | Boussignac et al. | 128/204.22 |
| 6,277,645 | B1 * | 8/2001 | Mault | 436/133 |
| 6,309,360 | B1 * | 10/2001 | Mault | 600/531 |
| 6,319,199 | B1 * | 11/2001 | Sheehan et al. | 600/200 |
| 6,358,215 | B1 * | 3/2002 | Ricciardelli | 600/532 |
| 6,367,475 | B1 * | 4/2002 | Kofoed et al. | 128/205.23 |
| 6,402,698 | B1 * | 6/2002 | Mault | 600/532 |
| 6,435,183 | B1 * | 8/2002 | Farman | 128/204.25 |
| 6,468,222 | B1 * | 10/2002 | Mault et al. | 600/531 |
| 6,478,736 | B1 * | 11/2002 | Mault | 600/300 |
| 6,506,608 | B2 * | 1/2003 | Mault | 436/133 |
| 6,526,802 | B1 | 3/2003 | Fisher et al. | |
| 6,582,376 | B2 * | 6/2003 | Baghdassarian | 600/543 |
| 6,585,662 | B1 * | 7/2003 | Jones et al. | 600/538 |
| 6,708,688 | B1 * | 3/2004 | Rubin et al. | 128/200.23 |
| 6,790,178 | B1 * | 9/2004 | Mault et al. | 600/300 |
| 6,824,520 | B2 * | 11/2004 | Orr et al. | 600/529 |
| 6,899,683 | B2 * | 5/2005 | Mault et al. | 600/531 |
| 6,915,705 | B1 * | 7/2005 | Truitt et al. | 73/861.52 |
| 6,935,338 | B1 * | 8/2005 | Triunfo, Jr. | 128/204.22 |
| 6,955,650 | B2 * | 10/2005 | Mault et al. | 600/531 |
| 7,059,322 | B2 * | 6/2006 | Rich et al. | 128/200.24 |
| 7,165,547 | B2 * | 1/2007 | Truitt et al. | 128/204.21 |
| 7,172,557 | B1 * | 2/2007 | Parker | 600/529 |
| 7,198,044 | B2 * | 4/2007 | Trueba | 128/200.16 |
| 2002/0077765 | A1 | 6/2002 | Mault | |
| 2002/0095096 | A1 * | 7/2002 | Mault | 600/531 |
| 2003/0167016 | A1 * | 9/2003 | Mault | 600/529 |
| 2004/0097820 | A1 * | 5/2004 | Bradley et al. | 600/529 |
| 2004/0204655 | A1 * | 10/2004 | Stock et al. | 600/532 |
| 2004/0249300 | A1 * | 12/2004 | Miller | 600/532 |
| 2004/0254491 | A1 * | 12/2004 | Ricciardelli | 600/529 |
| 2005/0009195 | A1 * | 1/2005 | Wang | 436/132 |
| 2006/0206034 | A1 * | 9/2006 | Stock et al. | 600/532 |
| 2007/0016092 | A1 * | 1/2007 | Shaw et al. | 600/532 |
| 2007/0100250 | A1 * | 5/2007 | Kline | 600/532 |
| 2007/0123792 | A1 * | 5/2007 | Kline | 600/538 |

FOREIGN PATENT DOCUMENTS

WO          03009751 A1    2/2003

* cited by examiner

HANDHELD BREATH TESTER HOUSING AND MOUTHPIECE

CROSS REFERENCE TO RELATED APPLICATIONS

This application claims priority to and the benefit of the filing dates of U.S. Provisional Application Nos. 60/462,122 filed on Apr. 10, 2003 and 60/525,423 filed on Nov. 26, 2003, both of which are hereby incorporated by reference in their entirety.

BACKGROUND OF THE INVENTION

This invention relates generally to breath testing devices, and more specifically, to a housing for a handheld breath tester.

Breath testing devices typically are used by police officers when assessing whether a driver has consumed an amount of alcohol in excess of the legal limit in that particular jurisdiction. Police officers have several concerns when performing an alcohol breath test, including safety. For safety reasons, an officer typically would prefer positioning himself in a sideways stance relative to the subject, and hold the breath testing device in one hand, i.e., hold the device using only his non-weapon hand outstretched towards the subject. In this position, a potentially belligerent subject is kept at arm's length and at the opposite side of the officer's weapon, so the subject cannot grab the officer or any of his equipment. Also, the officer's other hand is kept free and accessible to his gun or other non-lethal weapons that may be needed.

When in this position, the officer also can keep his face comfortably turned on the subject to observe the subject throughout the entire test. Specifically, there are generally subject-blowing cues on the display that the officer needs to observe while also observing the subject.

Further, during a test, a subject should not be able to view the device display. If the subject can view the display during a test, the subject may try to manipulate the manner of blowing, which may diminish the ability of the officer to get the best breath test result. Also, the subject's discard breath should not be directed at the officer for health reasons.

Breath testing devices typically include a removable mouthpiece. For health reasons, a new mouthpiece is used for each subject. Since much alcohol breath testing is done at night under less than ideal lighting conditions, the mouthpiece should mount to the housing in an easy and intuitive manner. Traditionally, mouthpieces have holes in the side of them, which are required to align with ports on the instrument housing. One port is provided so that breath is drawn into the internal fuel cell sensor and another port may be used to measure pressure in the mouthpiece for flow measurement of the breath. These ports mate with the holes in the mouthpiece with an airtight seal for proper instrument performance. Before starting a test, a clean mouthpiece must be oriented and lined up so the holes align properly with the ports and then pushed straight on. This is not always easily done under less than ideal lighting conditions. Also, the manner in which the mouthpiece is mounted is not necessarily intuitive and may require the officer's close observation.

Traditionally, handheld breath testers have the entire operator interface, including the display, on a broad face of the instrument. The interface also typically includes actuator buttons necessary for instrument operation, e.g., a "manual" sample button. The natural grip on these instruments is such that the officer can hold the unit in his hand and read the display and operate the buttons. The mouthpiece generally mounts on the top of the instrument such that the subject breath travels from left to right as one faces the display.

With many known handheld breath testers, the mouthpiece is parallel to the top of the instrument housing, which has a rectangular shape. No matter how the instrument is held by the officer, the display is substantially flat and is viewed at right angles to the run of the mouthpiece so that during use, the display and the mouthpiece are at roughly the same elevation with respect to the officer. Due to the straight mouthpiece, the mouthpiece extends from the subject's mouth perpendicular to the plane of the subject's face. This relative positioning works against natural viewing of the display by the officer and makes it more difficult for the officer to watch both the display and the subject easily and naturally.

With known breath testers, and to maintain the display in view of the officer, the officer typically stands to the side of the subject. In this position, the officer compromises his ability to keep the subject in plain view in front of him and is positioned less than a full arm's length from the subject. The subject also has some opportunity to view the display. If the officer moves away from the subject, this compromises the officer's view of the display and the subject's discard breath may be directed towards the officer.

Some known devices provide a mouthpiece that swivels on the top of the device housing so that the officer can stand in front of the subject, however, the officer is not able to stand in a sideways stance relative to the subject. Further, in this position, the subject's discard breath is directed toward officer. Other known devices direct the subject's breath out the back of the instrument, however, such devices do not enable an officer to directly view the display while in a sideways stance.

Also, known handheld breath testers generally are designed to be held in the right hand of the officer with the subject blowing into the mouthpiece from the left. Left-handed officers generally hold the instrument in their right hand. If the officer holds the device in his left hand, it is nearly impossible for the officer to view the display while the subject has opportunity to view the display.

Some known devices provide that the mouthpiece can be mounted to the top of the device housing in two ways to facilitate left or right hand use. However, neither mounting allows the officer to stand in a sideways stance while viewing of subject and display nor directs the subject's discard breath away from the officer while the officer tries to administer the test in a sideways stance. Further, it is not necessarily intuitive as to how to mount the mouthpiece for best left or right hand use.

Some known breath testers allow an officer to take a manual sample instead of an automatic sample. Specifically, a manual sample is taken by the officer depressing a button on the device rather than having the device automatically determine a time at which to take the sample. A manual sample may be taken if a subject has a lung impairment or is being belligerent. To effectively take a manual sample, the officer must be keenly observing the subject and the instrument display in order to judge the situation so that in real time, he may make the decision to take the sample. If the officer does not select an appropriate time to take the sample, the officer may lose his best opportunity to get a reading at all. Known instruments do not enable both manual and automatic samples with officer standing in the position described above.

BRIEF DESCRIPTION OF THE INVENTION

In one aspect, a breath tester housing is provided. The housing comprises a base to be gripped by an operator, a display oriented to be in line with an operator's direct line of view while gripping the base, and a mouthpiece interface for interfacing with a removable mouthpiece so that when a subject blows into the mouthpiece, the display is not in the direct line of view of the subject.

In another aspect, a mouthpiece for a breath tester is provided. The mouthpiece includes a first end, a second end, and a body extending therebetween. The body has a substantially D-shaped cross-sectional shape. One of the body first end and second end is closed, and the remaining body end is open to enable a subject being tested to blow air into the tube. The body includes at least one port for channeling air blown into the mouthpiece therethrough.

In yet another aspect, a breath tester housing assembly is provided. The assembly comprises a housing having a base to be gripped by an operator, a display oriented to be in line with an operator's direct line of view while gripping the base, and a mouthpiece interface for interfacing with a removable mouthpiece so that when a subject blows into the mouthpiece, the display is not in the direct line of view of the subject. The assembly further comprises a mouthpiece for engaging to the mouthpiece interface. The mouthpiece comprises a body having a substantially planar surface.

DETAILED DESCRIPTION OF THE INVENTION

Figure 1:
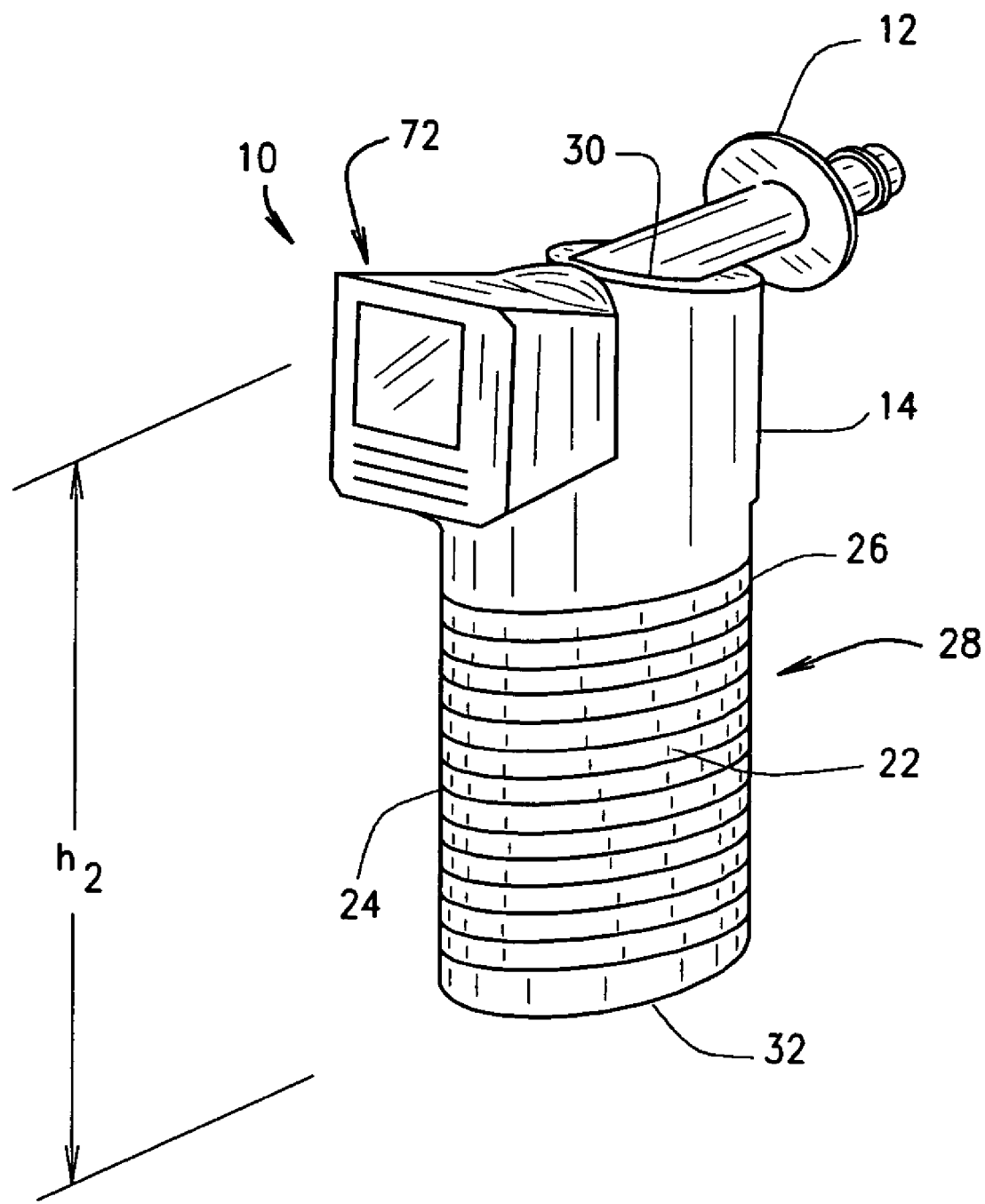
FIG. 1 is a front perspective view of an exemplary embodiment of a hand-held breath testing device housing assembly, including a housing and a mouthpiece coupled to the housing in a testing position.
Figure 2:
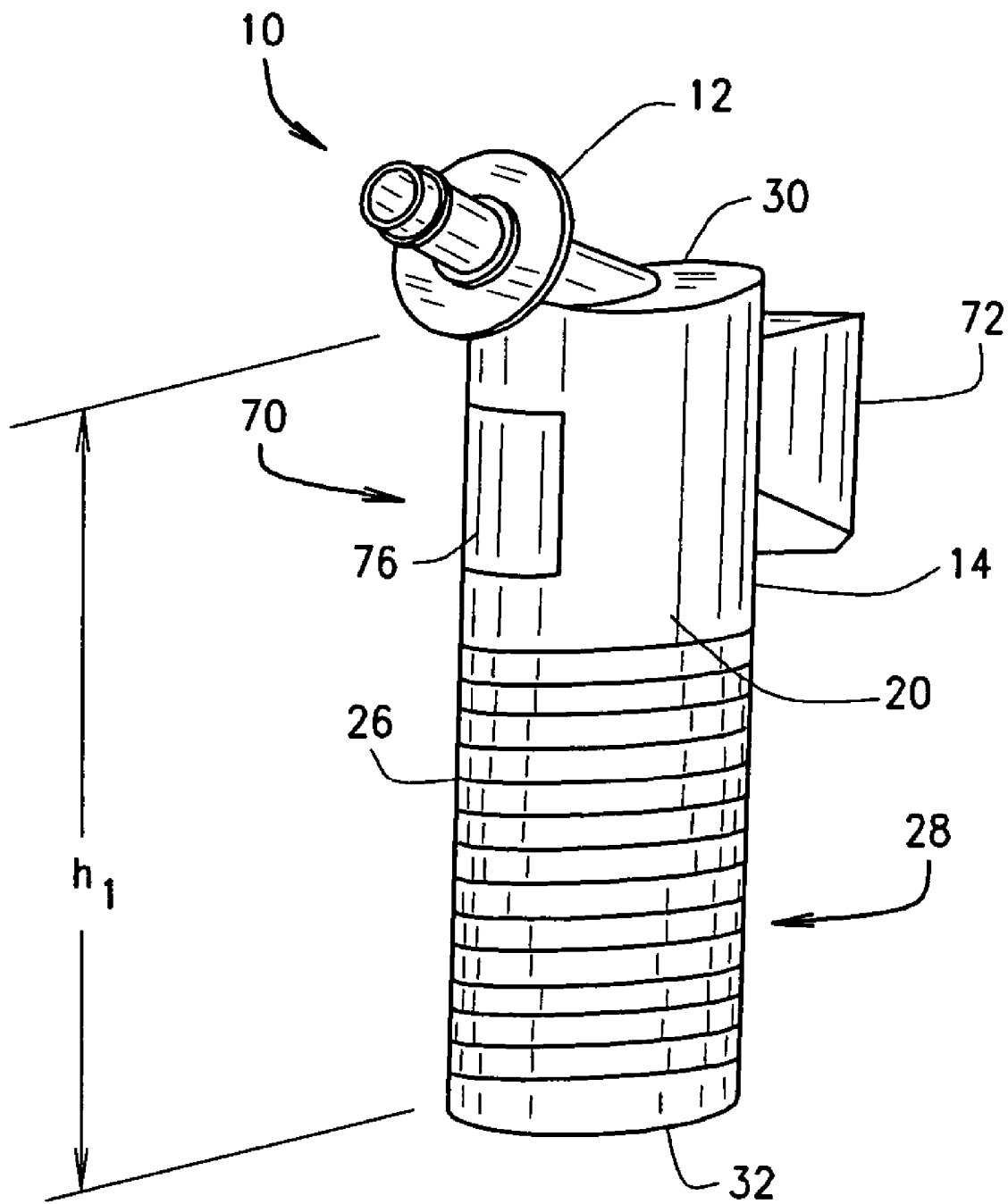
FIG. 2 is a rear perspective view of the housing assembly shown in FIG. 1.
Figure 3:
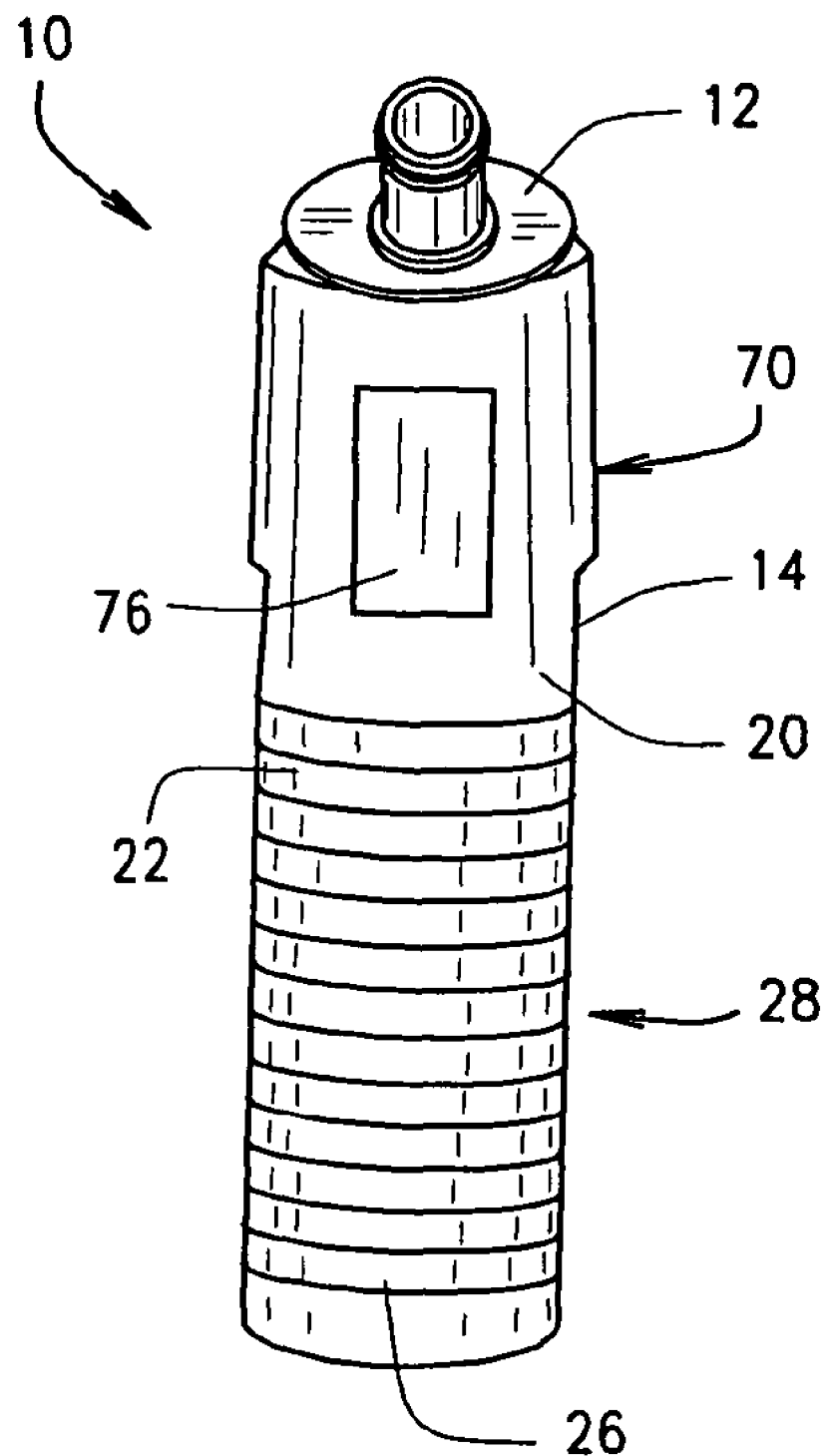
FIG. 3 is a rear view of the housing assembly shown in FIG. 1.
Figure 4:
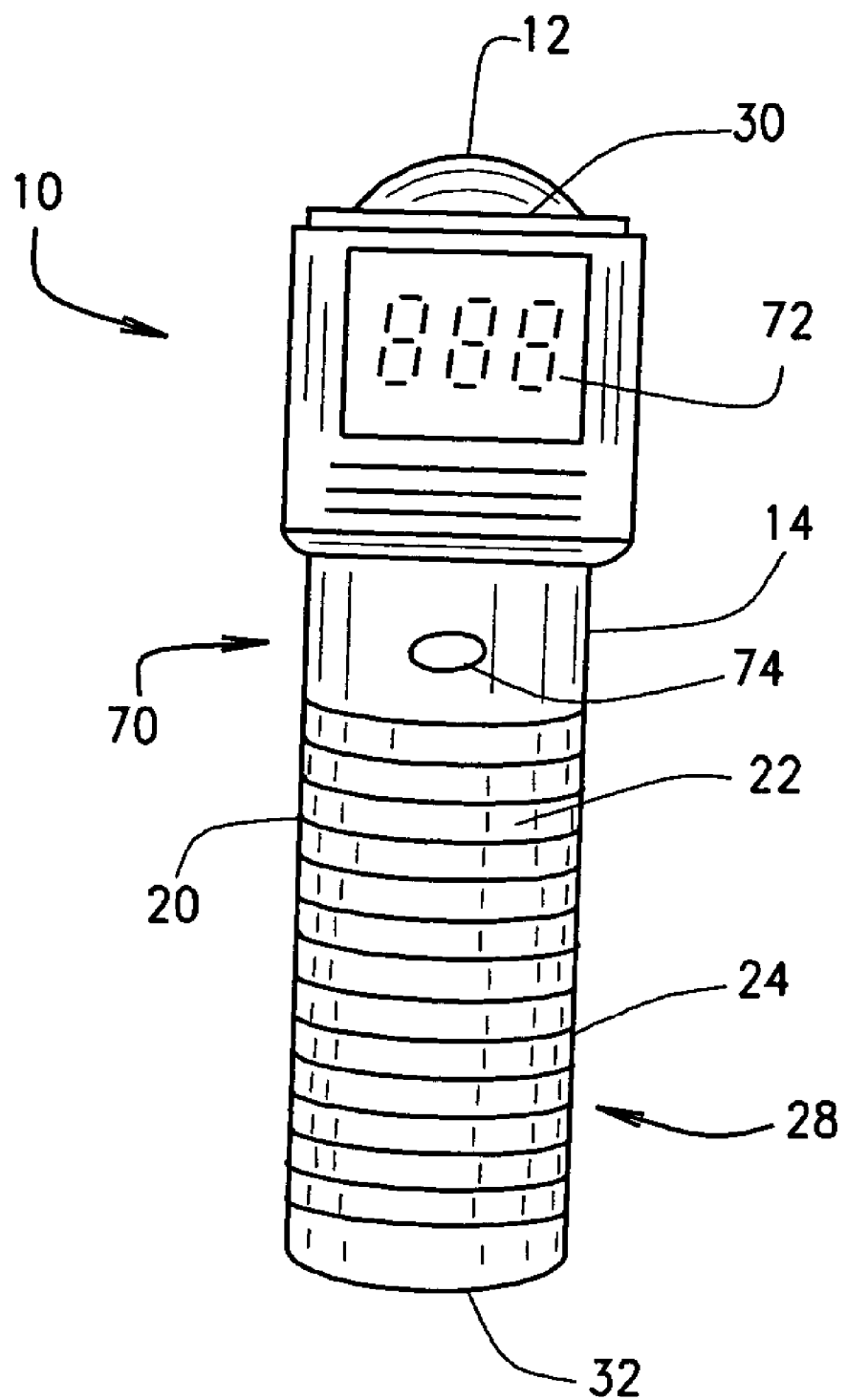
FIG. 4 is a front view of the housing assembly shown in FIG. 1.
Figure 8:
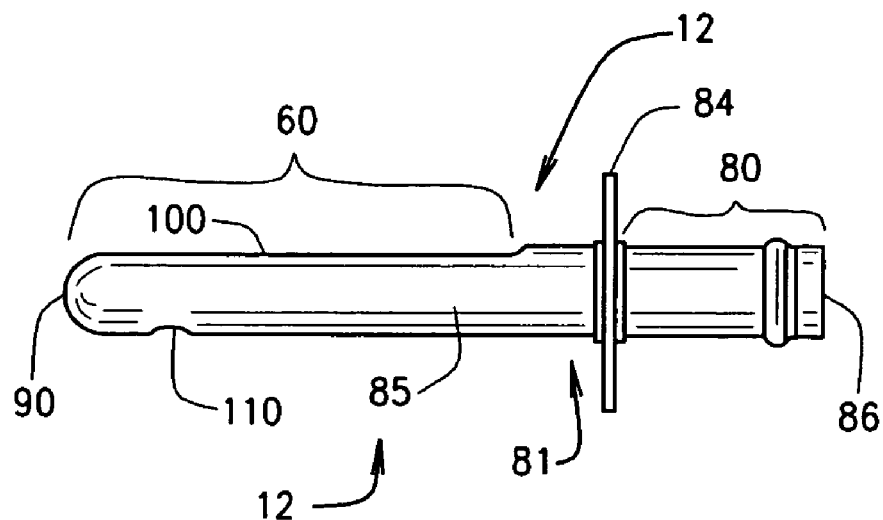
FIG. 8 is a side view of the mouthpiece shown in FIG. 6.
Figure 5:
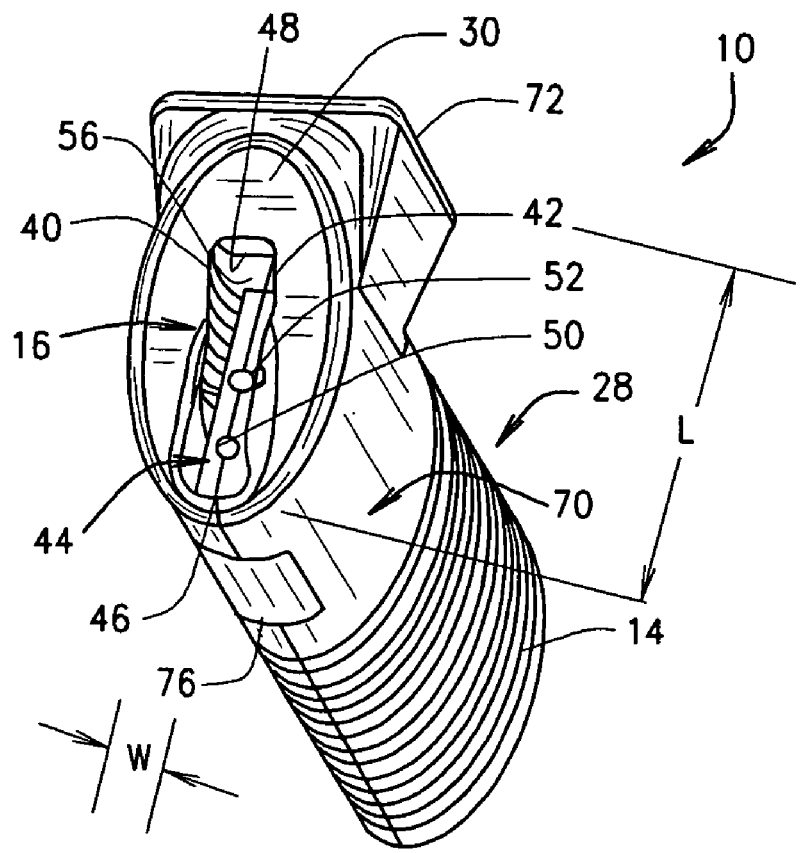
FIG. 5 is a top perspective view of the housing shown in FIG. 1.
Figure 6:
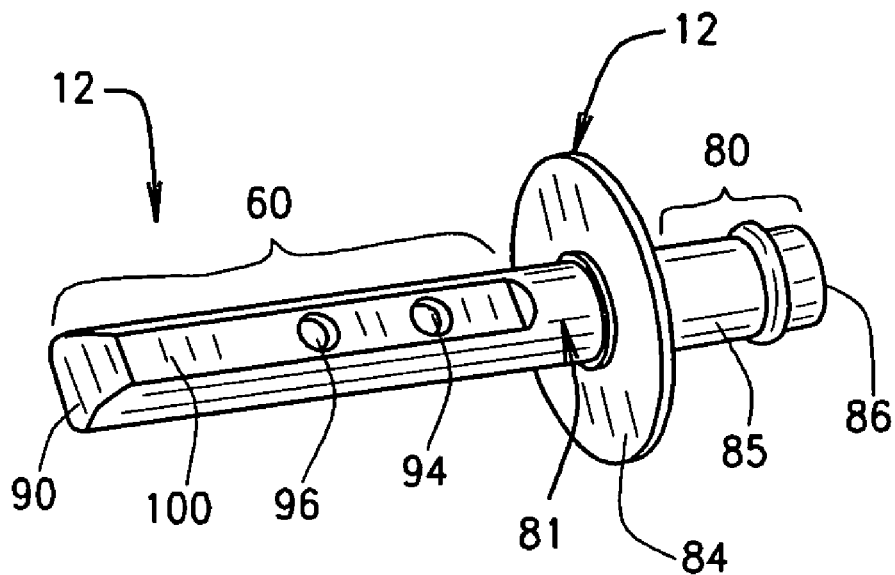
FIG. 6 is a perspective bottom view of an exemplary embodiment of the mouthpiece shown in FIGS. 1-4.
Figure 7:
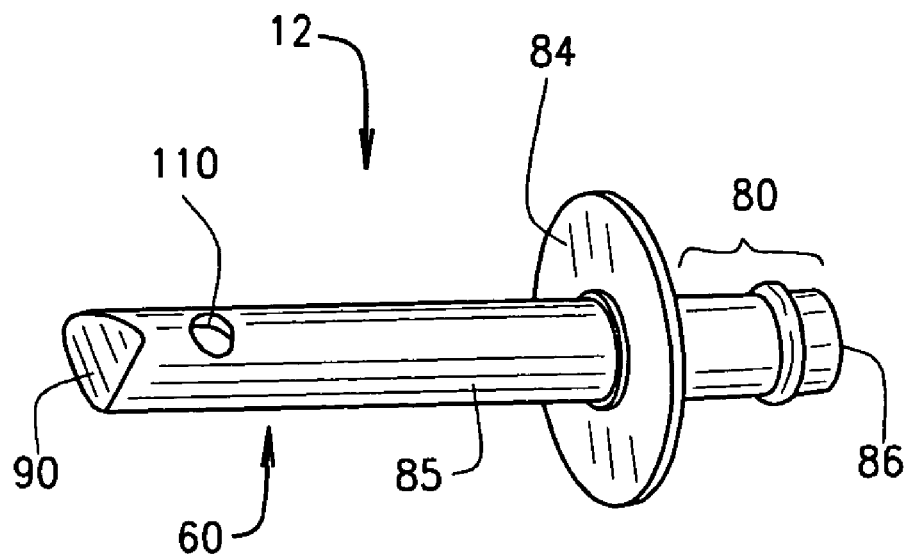
FIG. 7 is a perspective top view of the mouthpiece shown in FIG. 6.

An exemplary embodiment of a breath testing device housing assembly 10 is shown in FIGS. 1-4. Assembly 10 includes a mouthpiece 12 and a housing 14. Specifically, FIG. 1 is a front perspective view of breath testing device housing 14 including a mouthpiece 12 coupled thereto in a testing position, and FIG. 2 is an opposite rear perspective view of housing assembly 10. FIG. 3 is a rear view of housing assembly 10, and FIG. 4 is a front view of housing assembly 10. FIG. 5 is a top perspective view of housing 14. FIGS. 6 and 7 are perspective bottom and top views, respectively, of mouthpiece 12, and FIG. 8 is a side view of mouthpiece 12.

Breath testing device housing 14 includes a mouthpiece interface 16. Housing 14 is symmetrically-formed and includes a pair of opposed sidewalls 20 and 22 that are connected together along a front edge 24 and an axially-spaced rear edge 26, such that a cavity is defined therebetween. Electronic components of the breath testing device are housed within housing 14. Sidewalls 20 and 22 form a base 28 for housing 14 and each extends radially between a top surface 30 and a bottom surface 32. In the exemplary embodiment, housing base 28 has a substantially elliptical cross-sectional profile. In alternative embodiments, housing base 28 has a non-elliptical cross-sectional profile.

The elliptical profile of housing base 28 facilitates housing assembly 10 being gripped in an operator's hand such that a thumb of the operator or officer performing the breath test is positioned generally against front edge 24, while the remaining fingers of the operator are positioned generally against rear edge 26. Moreover, because housing 14 is symmetrical, housing assembly base 28 accommodates both right- or left-handed operator use.

In the exemplary embodiment, each sidewall 20 and 22 extends arcuately between front and rear edges 24 and 26. Moreover, bottom surface 32 is substantially planar, and extends substantially perpendicularly between sidewalls 20 and 22, and between front and rear edges 24 and 26, respectively. Top surface 30 also extends between sidewalls 20 and 22, and extends obliquely between edges 24 and 26 with respect to bottom surface 32. Accordingly, in the exemplary embodiment, front edge 24 has a height $h_1$ measured between top and bottom surfaces 30 and 32, respectively, that is less than a height $h_2$ of rear edge 26. In an alternative embodiment, rear edge 24 and front edge 26 each have approximately the same height.

In the exemplary embodiment, mouthpiece interface 16 is defined within top surface 30 and includes a pair of opposed sidewalls 40 and 42 that are spaced apart such that a receiver or channel 44 is defined therebetween. In alternative embodiments, mouthpiece interface 16 may have other cross-sectional profiles or configurations that enable mouthpiece interface 16 to receive a mouthpiece 12 in sealing contact such that mouthpiece 12 and mouthpiece interface 16 function as described herein. Channel 44 is also bordered by a bottom surface 46 and a rear wall 48 that each extend between channel sidewalls 40 and 42. Bottom surface 46 is substantially planar and includes a pair of ports 50 and 52. In alternative embodiments, bottom surface 46 is non-planar and has a contour that substantially conforms to at least a portion of mouthpiece 12, as described in more detail below. Ports 50 and 52 extend radially into breath tester housing 14 for channeling air towards the breath testing device components housed within housing 14. Specifically, in the exemplary embodiment, port 52 provides airflow into, for example, a fuel cell for sampling, and port 50 provides airflow to a flow sensor. The sensor may be, but is not limited to being, a flow meter, a pressure sensor and/or a thermistor.

In the exemplary embodiment, mouthpiece interface 16 also includes a lens 56 in at least one channel sidewall 40 and/or 42 that enables light to pass from an interior of housing 14 into channel 44 to partially illuminate channel 44. In other embodiments, mouthpiece interface 16 includes an opening rather than lens 56, and light simply passes through the opening into channel 44. Of course, more than one lens 56 or more than one opening can be used to illuminate channel 46. In another alternative embodiment, mouthpiece interface 16 includes a light source (not shown) that may be selectively activated to illuminate at least a portion of channel 44. In a further alternative embodiment, any of sidewalls 40 or 42, rear wall 48, and/or bottom surface 46 may be formed with a lens, an opening, and/or with a light source.

In the exemplary embodiment, mouthpiece interface 16 is positioned such that channel bottom surface 46 is obliquely oriented with respect to housing bottom surface 32. In other embodiments, mouthpiece interface is positioned to receive channel bottom surface 46 in other orientations with respect to housing 14, such as for example, parallel to top surface 30. More specifically, as described in more detail below, when looking at the broad face of housing sidewall 22, mouthpiece interface channel bottom surface 46 rises from left to right.

Channel rear wall 48 extends arcuately between channel sidewalls 40 and 42 such that rear wall 48 forms a rounded inner wall, or dead end, that facilitates receiving and aligning mouthpiece 12 within channel 44, as is described in more detail below. Channel 44 has a width W and a length L, and is substantially centered between housing sidewalls 20 and 22. In the exemplary embodiment, channel width W is sized approximately the same as, or slightly smaller than, a corresponding width $W_1$ of mouthpiece 12, and length L is approximately the same length as a corresponding length $L_1$ of a coupling portion 60 of mouthpiece 12. Accordingly, in the exemplary embodiment, channel 44 is sized to receive mouthpiece 12, as described in more detail below, in a "snap-fit", and in a proper orientation, such that once mouthpiece 12 is removably coupled within channel 44, sealing contact is created between mouthpiece 12 and channel bottom surface 46.

More specifically, in the exemplary embodiment, mouthpiece interface 16 is formed from molded plastic, such that as mouthpiece 12 is inserted within channel 44, sidewalls 40 and 42 flex outwardly, and are then returned to their original position around the rounded profile of mouthpiece 12. Accordingly, a spring-like force induced by sidewalls 40 and 42 facilitates retaining mouthpiece 12 within interface 16. In an alternative embodiment, sidewalls 40 and 42 are substantially rigid and rather at least a portion of mouthpiece interface 16 is flexible and deformable during insertion of mouthpiece 12 within channel 44. To facilitate additional retention of mouthpiece 12 within interface, in the exemplary embodiment, sidewalls 40 and 42 are formed slightly rounded such that each extends arcuately upward from channel bottom 46. Alternatively, other cross-sectional profiles may be defined by channel sidewalls 40 and 42, and bottom surface 46.

Housing 14 also includes at least one actuator 70 and a display 72. More specifically, in the exemplary embodiment, housing 14 includes a light illumination actuator 74 and a manual sample actuator 76. In the exemplary embodiment, actuators 70, 74, and 76 are depressible buttons. In an alternative embodiment, actuator 74 may be positioned immediately below and adjacent to display 72. Manual sample actuator 76 is centered along housing rear edge 26, and display 72 is centered opposite sample actuator 76 and along front edge 24. Alternatively, either actuator 70 and/or display 72 may be offset from a respective housing edge 26 or 24. It should also be noted that in alternative embodiments, optics or other technology could be used to place the effective display as described, whereas the true display may be remote from that location. Moreover, in another embodiment, actuators 70 may be positioned along sidewalls 20 and/or 22. In the exemplary embodiment, depressing manual sample actuator 76 enables an operator performing a breath test to take a manual sample, rather than an automatic sample. Display 72 enables the results of breath testing to be visually displayed to the operator during the breath testing. Depressing light illumination actuator 74 causes display 72 to be internally illuminated during a breath test, and also causes at least a portion of channel 44 to be at least partially illuminated when mouthpiece 12 is being coupled within interface 16. In an alternative embodiment, mouthpiece interface 16 does not include lens 56, and rather, light at least partially illuminates channel 44 through any of sidewalls 40 or 42, rear wall 48, and/or bottom surface 46, or through interfaces defined adjacent walls 40, 42, 48, or 46 within channel 44.

In the exemplary embodiment, mouthpiece 12 is a hollow tube that includes coupling portion 60, an insertion portion 80, and a substantially cylindrical portion 81 extending therebetween. Alternatively, mouthpiece 12 may be any configuration or device, and is not limited to being a tubular configuration, that facilitates channeling a subject's breath into housing 14 and towards a sensor, as described herein. As described above, coupling portion length $L_1$ enables mouthpiece 12, as described in more detail below, to be fully inserted within interface 16. Insertion portion 80 is hollow and provides an airflow passage that is inserted in a person's mouth being tested. In the exemplary embodiment, a stop 84 extends radially outward from an outer surface 85 of mouthpiece 12 and limits the amount of mouthpiece 12 that may be inserted within the person's mouth. More specifically, insertion portion 80 extends from stop 84 to an inlet end 86 of mouthpiece 12. In the exemplary embodiment, insertion portion 80 has a substantially circular cross-sectional profile. In alternative embodiments, mouthpiece 12 does not include stop 84. It should be noted that mouthpiece insertion portion 80 is not limited to having a substantially circular cross-sectional profile, but rather, insertion portion 80 may be any shape or configuration that facilitates channeling air from the subject towards coupling portion 80, such as, but not limited to a reed-like configuration, and/or a non-circular cross-sectional profile.

Coupling portion 60 is also hollow and extends from body portion 81 to a radially inner end 90 of mouthpiece 12. Inner end 90 is rounded and is sealed such that airflow entering inlet end 86 is channeled through a pair of ports 94 and 96 into channel ports 50 and 52 and into the breath testing device. Coupling portion 60 has a cross-sectional profile that substantially mirrors at least a portion of the cross-sectional profile defined within at least a portion of channel 44. As such, coupling portion 60 is essentially "murphy-proofed" such that the cross-sectional profile of portion 60 facilitates mouthpiece 12 being received only in the proper orientation within channel 44. Accordingly, in the exemplary embodiment, coupling portion 60 includes a radially inner surface 100 that is substantially planar, such that in the exemplary embodiment, coupling portion 60 has a substantially D-shaped cross-sectional profile. It should be noted that coupling portion 60 is not limited to having a substantially D-shaped cross-sectional profile, but rather, coupling portion 60 may have cross-sectional shape that enables coupling portion 60 to function as described herein, such as, but not limited to a substantially circular cross-sectional profile, and/or a frusto-conical cross-sectional profile. Specifically, the combination of the cross-sectional profiles of coupling portion 60 and channel 44, and the substantially mating contours of coupling portion 60 and channel bottom surface 46, facilitates sealing contact being maintained between coupling portion 60 and channel bottom surface 46 when mouthpiece 12 is coupled within interface 16. In an alternative embodiment, mouthpiece 12 and channel bottom surface 46 are in contact such that sealing contact is created between sidewalls defining ports 50 and 52 and mouthpiece ports 94 and 96, respectively.

Coupling portion 60 also includes a discard breath port 110 that discharges discarded breath from the breath testing device. More specifically, and as described in more detail below, the combination of channel 44 and coupling portion 60 enables mouthpiece 12 to be oriented such that the test subject's discarded breath is not discharged through port 110 towards the operator performing the breath testing. In an alternative embodiment, discard breath port 110 could be located, but is not limited to being located, anywhere along a side, top, or bottom of mouthpiece 12.

During use, initially a detachable mouthpiece 12 is coupled to housing 14. The method of mouthpiece insertion is intuitive to the operator without the use of a manifold and clearly snaps into a "home" or "testing" position with no ambiguity. The instrument mouthpiece receiver 44 is dead-ended, and the mouthpiece 12 itself has a blunt closed end 90, which is simply placed against the dead end 48 of receiver 44. Because channel 44 is rounded at wall 48, as is mouthpiece end 90, mouthpiece 12, although D-shaped in cross section, can only be pivotally coupled within channel 44 in one orientation with respect to housing 14. More specifically, because mouthpiece end 90 is rounded or "toe-shaped", once mouthpiece 12 is coupled within receiver 44, mouthpiece 12 can be rotated downward without end 90 coming out of channel 44. In other words, once mouthpiece end 90 is coupled within receiver 44 and adjacent dead end 48, mouthpiece end 90 is trapped in a loose, but effective pivot. Moreover, in the exemplary embodiment, lighting in receiver 44 facilitates reducing ambiguity in inserting mouthpiece 12 during testing in poorly illuminated ambient conditions.

Mouthpiece 12 is then pivoted downward towards housing channel 44, such that ports 94 and 96 are aligned with, and engage channel ports 50 and 52 as mouthpiece 12 is coupled into housing channel 44. More specifically, although the ports 50 and 52 on the housing mate with the mouthpiece ports 94 and 96 at an angle (due to the pivoting action), the substantially planar bottom surfaces of mouthpiece 12 and channel 44 facilitates sealing between the ports 50 and 94, and between ports 52 and 96. Moreover, since the mouthpiece 12 has a D-shaped cross-sectional profile, orientation is intuitive. More specifically, in the exemplary embodiment, because channel sidewalls 40 and 42 are rounded past center, when mouthpiece 12 nears the end of its pivoting motion, it forces sidewalls 40 and 42 outward, working against the spring force of the molded plastic sidewalls, and then snaps within channel 44, walls 40 and 42 return to their original position and extend somewhat around the rounded mouthpiece 12. In an alternative embodiment, sidewalls 40 and 42 are substantially rigid and rather mouthpiece insertion portion 80 is flexible and deformable during insertion of mouthpiece 12 within channel 44.

When the mouthpiece 12 is in the subject's mouth, the mouthpiece 12 exits the mouth at a right angle to the plane of the subject's face, and as such the display 72 is tipped up towards the eyes of the officer. Thus, when the officer holds assembly 10 in the natural and intuitive manner in the subject's mouth, the officer is easily able to keep the subject in plain view while comfortably monitoring display 72 at the same time. Moreover, because housing 14 includes a display 72 and actuators 70 that are along the same axis, the display 72 and actuators 70 are also aligned with the operator's or officer's view while holding assembly 10 in the intuitive and natural position. Moreover, unlike other known devices, display 72 and actuators 70 are on the edges 24 and 26 of assembly. Accordingly, when assembly 10 is held in the natural and intuitive manner in an outstretched arm, display 72 is directly in the line-of-sight of the officer, and mouthpiece 12 points to the subject, thus accommodating the officer's need to be in the preferred position while administering the breath test. More specifically, the display 72 and subject being tested are both in line and in his view, one in front of the other. As such, the subject cannot see the display 72, and the breath discharged from the mouthpiece 12 is channeled upward through discard breath port 110, such that the subject's discard breath is not directed at the officer.

In addition, because housing 14 is symmetrical, housing 14 accommodates both right or left handed use. Moreover, the cross-sectional shape of mouthpiece 12 and channel 44 enables mouthpiece 12 to only mount one way in an intuitive manner, whether housing 14 is grabbed with the operator's left or right hand. Accordingly, the natural and intuitive way to hold assembly 10 in either case is with the arm outstretched, mouthpiece 12 pointed toward the subject, and display 72 pointed towards the officer and tipped up towards the officer's eyes.

Manual sample actuator 76 is located on housing edge 26 and is opposite display 72. It should be noted that alternatively, manual actuator 76 could be repositioned to be made to naturally operate with a finger other than the operator's forefinger.

Thus, while the officer is standing with subject and display 72 in his direct field of view, he may at any time press manual actuator 76 with his forefinger without compromising or slacking his grip in any way. This allows for a complete one-handed use that is natural and intuitive whether using the left or right hand to take a manual sample. The manual sample actuator 76, and any other actuator 70, can be located on either edge 24 or 26 of housing 14, such that the actuators 70 are positioned to provide for a true right/left-handed use of the instrument. Of course, in alternative embodiments, the actuators and/or the functions associated with each actuator can vary from the example embodiment described herein.

When testing is completed, the mouthpiece 12 is removed and discarded. To facilitate removal of the mouthpiece 12 from housing 14, in one embodiment, a mouthpiece ejector is utilized to displace the mouthpiece from the home position. For example, the mouthpiece ejector could be, but is not limited to being, spring loaded or biased with a release, that is selectively operable either manually, or by depressing an actuator.

In the exemplary embodiment, because mouthpiece 12 extends outwardly from housing 14, mouthpiece inlet end 86 may be tapped against a generally solid surface, such as, for example, a roof of a car, a table, or a leg of the tester's leg, to forcibly eject mouthpiece 12 from housing 14 without requiring an operator to physically touch the unsanitary mouthpiece inlet end 86. More specifically, when such an action is taken, mouthpiece 12 rotates out of position in a rotational direction that is opposite the direction of rotation of mouthpiece 12 during insertion of mouthpiece 12 within housing 14, without inducing any undue pressure to inlets 50 and 52, and without damaging housing 14.

Figure 9:
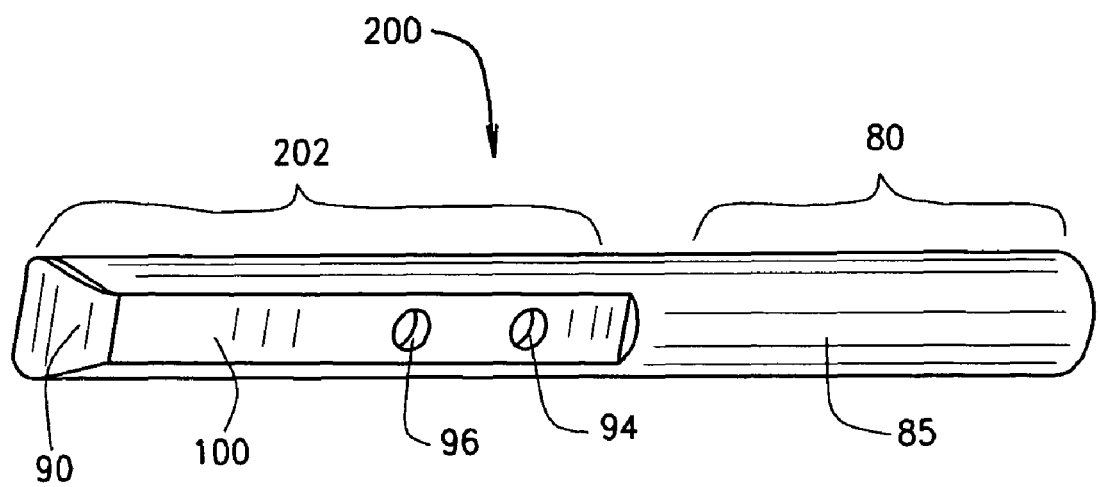
FIG. 9 is a perspective bottom view of a portion of an alternative embodiment of a mouthpiece that may be used with the housing shown in FIGS. 1-4.
Figure 10:
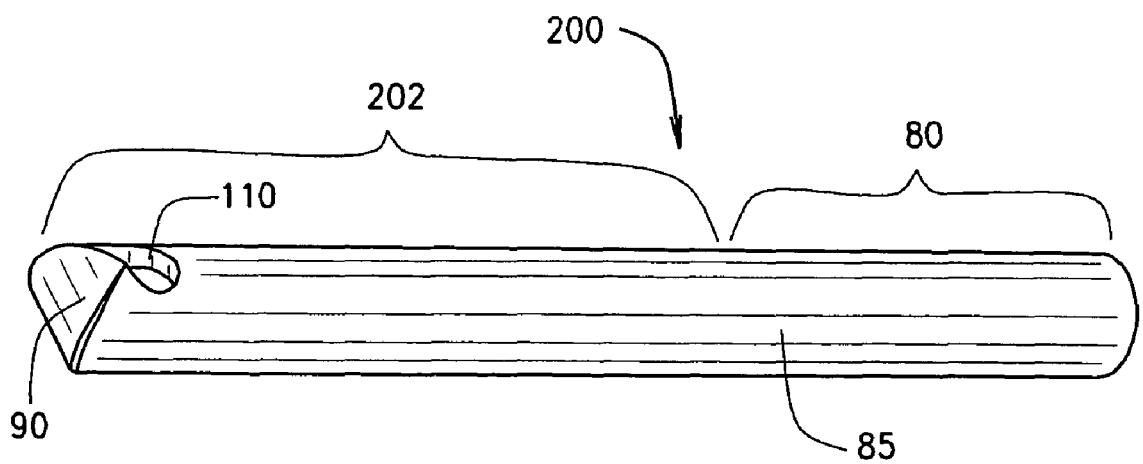
FIG. 10 is a perspective top view of the portion of the mouthpiece shown in FIG. 9.

FIG. 9 is a perspective bottom view of a portion of an alternative embodiment of a mouthpiece 200 that may be used with housing 14, and FIG. 10 is a perspective top view of mouthpiece 200. Mouthpiece 200 is substantially similar to mouthpiece 12 shown in FIGS. 6-8 and components in mouthpiece 200 that are identical to components of mouthpiece 12 are identified in FIGS. 9 and 10 using the same reference numerals used in FIGS. 6-8. Specifically, mouthpiece 200 includes insertion portion 80 that extends from mouthpiece inlet end 86 to a coupling portion 202. Coupling portion 202 is substantially similar to coupling portion 60 (shown in FIGS. 6-8) and has a substantially D-shaped cross-sectional profile. In alternative embodiments, coupling portion 202 has other cross-sectional profiles, such as, but not limited to, a substantially V-shaped cross-sectional profile.

Figure 11:
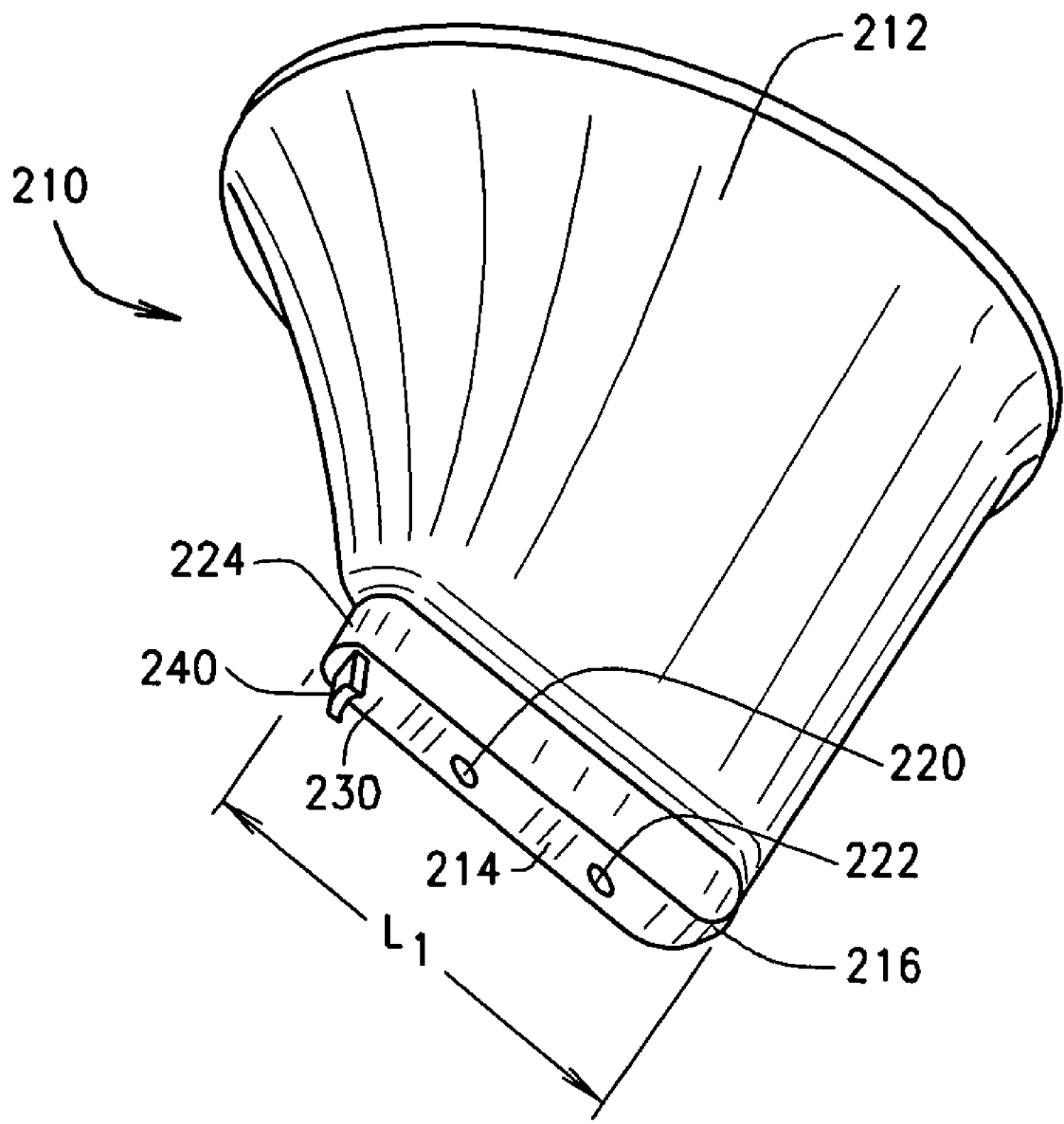
FIG. 11 is a perspective view of another alternative embodiment of a passive sampling cup that may be used with the housing shown in FIGS. 1-5.

FIG. 11 is a perspective view of another alternative embodiment of a passive sampling cup 210 that may be used with housing assembly 10 (shown in FIGS. 1-5). Portions of passive sampling cup 210 are substantially similar to portions of mouthpiece 12 shown in FIGS. 6-8. Passive sampling cup 210 is used for passive testing and includes a funnel portion 212 that extends outward from a coupling portion 214. Coupling portion 214 is substantially similar to coupling portion 60 (shown in FIGS. 6-8) and has a length $L_1$ that enables coupling portion 214 to be coupled within interface 16. Similarly to coupling portion 60, coupling portion 214 is also hollow and extends from funnel portion 212 to a radially inner end 216 of passive sampling cup 210. Inner end 216 is rounded and is sealed such that airflow entering funnel portion 212 is channeled through a pair of ports 220 and 222 into channel ports 50 and 52 (shown in FIG. 5) and into the breath testing device. In addition, waster air is discharged from sampling cup 210 through a waste air port 224 that facilitates ensuring that a flow of sample air is maintained into funnel portion 212. Coupling portion 214 also includes a radially outer surface 230 that facilitates a snap fit between passive sampling cup 210 and channel 44. In alternative embodiments, coupling portion 214 is formed with other cross-sectional profiles.

In the exemplary embodiment, coupling portion 214 also includes an alignment tab 240 that facilitates orienting sampling cup 210 with respect to assembly 10. More specifically, tab 240 ensures that cup 210 can only be coupled to assembly 10 such that ports 50 and 52 are properly aligned with respect to cup 210. In the exemplary embodiment, when coupling portion 214 is coupled to assembly 10, tab 240 extends along housing edge 26.

Figure 12:
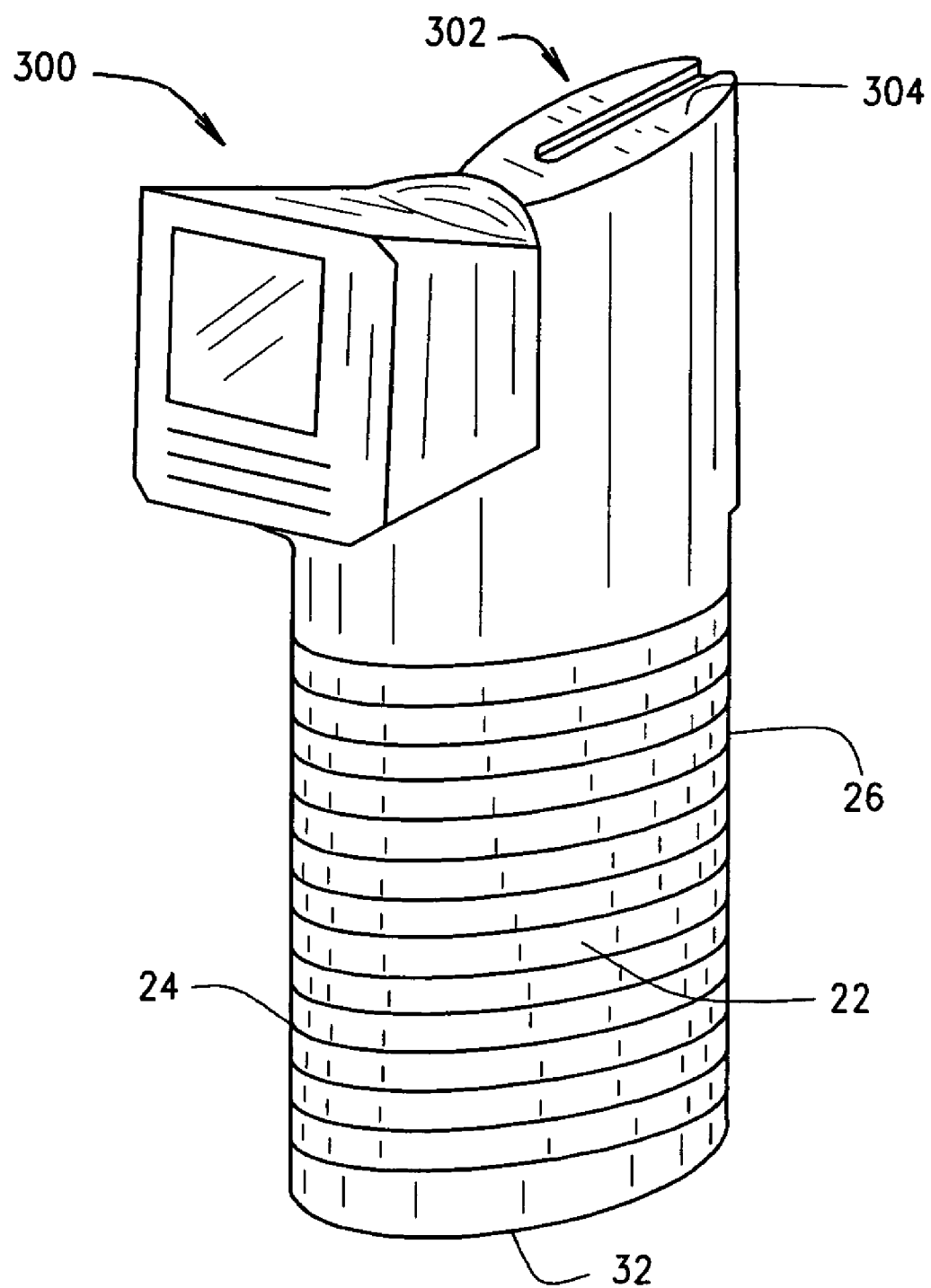
FIG. 12 is a side view of an alternative housing that may be used with the breath testing housing assembly shown in FIG. 1.

FIG. 12 is a side view of an alternative housing 300 that may be used with breath testing housing assembly 10 (shown in FIGS. 1-5) Housing 300 is substantially similar to housing 14 (shown in FIGS. 1-5) and components in housing 300 that are identical to components of housing 14 are identified in FIG. 12 using the same reference numerals used in FIGS. 1-5. Housing 300 is symmetrical and includes sidewalls 20 and 22 and a mouthpiece interface 302. Sidewalls 20 and 22 extends radially between a top surface 304 and bottom surface 32. Top surface 304 extends between sidewalls 20 and 22, and extends obliquely between edges 24 and 26 with respect to bottom surface 32.

In the exemplary embodiment, mouthpiece interface 302 is positioned such that channel bottom surface 46 (shown in FIG. 5) is obliquely oriented with respect to housing bottom surface 32, and is substantially parallel to top surface 30. More specifically, when looking at the broad face of housing sidewall 22, mouthpiece interface channel bottom surface 46 rises from left to right.

Exemplary embodiments of breath testing housing assemblies are described above in detail. The assemblies are not limited to the specific embodiments described herein, but rather, components of each assembly may be utilized independently and separately from other components described herein. For example, there are a variety of ways to shape a mouthpiece such that it has a blunt, closed end that is easily oriented in a pivot, such that its movement is angular as it approaches the instrument ports, has a substantially planar surface around the mating holes, and snaps into the "home" position. Accordingly, the mouthpiece could be partially V-shaped in cross section for orientation during insertion into the pivot as well as to facilitate movement past the side walls of the mouthpiece receiver. Moreover, there could be a substantially planar area at the bottom of the "V" in order to facilitate sealing on the ports. In such an embodiment, the receiver walls may not extend arcuately from the receiver bottom surface.

In addition, although in the described embodiment, the angular movement of the mouthpiece is in a substantially vertical plane when the instrument is in the upright position, in alternative embodiments, the mouthpiece could be moved in a horizontal plane or at some other angular orientation as well. Furthermore, instead of the "toe" of the mouthpiece being the direct pivot point, alternate pivot points could be formed on the sides of the mouthpiece, and/or fitted to a shape on the receiver, in order to get the same type of angular mouthpiece movement.

Furthermore, although the mouthpiece is described has having only two ports, in alternative embodiments, the mouthpiece could have more or less than two ports depending on the desired application. Moreover, the second port does not have to be a pressure port, but rather the second port could be used to allow air to flow to a thermistor mounted to a pin that extends into the mouthpiece to measure flow, while remaining sealed around the pin. In addition, there could be similar ports for measuring breath temperature or some other relevant phenomenon.

While the invention has been described in terms of various specific embodiments, those skilled in the art will recognize that the invention can be practiced with modification within the spirit and scope of the claims.

What is claimed is:

1. An alcohol breath testing device housing for a breath tester for use by an operator to test a subject, the housing comprising:
    a base to be gripped by the operator and having a front edge and a back edge opposite said front edge;
    a display disposed on the front edge of the base;
    a mouthpiece interface receiving a removable mouthpiece, said mouthpiece interface being oriented with respect to said base such that when a mouthpiece is coupled thereto, the mouthpiece extends outward from said back edge, and said mouthpiece interface being oriented with respect to said base such that when the operator stands in front of the subject and the subject blows into the mouthpiece, said display is in the direct line of view of the operator and not in the direct line of view of the subject;
    the mouthpiece interface comprising a generally U-shaped channel sized to receive the mouthpiece therein, the mouthpiece being configured to be pivotally coupled into the mouthpiece interface;
    a manual sample button located on the back edge of said base opposite the display; and
    an alcohol sensor fluidly connected to the mouthpiece interface, the alcohol sensor being adapted to detect alcohol present in the subject from a breath sample obtained by the subject blowing into the mouthpiece.

2. An alcohol breath testing device housing in accordance with claim 1 wherein said housing comprises a first sidewall, an opposite second sidewall coupled to the first sidewall at the front edge and the back edge, a top surface, and a bottom surface, said mouthpiece interface being located on said top surface.

3. An alcohol breath testing device housing in accordance with claim 2 wherein said first and second sidewalls of the housing are symmetrical.

4. An alcohol breath testing device housing in accordance with claim 2 wherein said mouthpiece interface is oriented such that when a mouthpiece is coupled thereto, the mouthpiece extends outward from said back edge.

5. An alcohol breath testing device housing in accordance with claim 2 wherein said mouthpiece interface is further oriented such that when the mouthpiece is coupled thereto, the mouthpiece extends at least one of obliquely from said top surface and substantially parallel to said top surface.

6. An alcohol breath testing device housing in accordance with claim 1 wherein discard breath is not directed at the operator.

7. An alcohol breath testing device housing in accordance with claim 1 further comprising at least one of a light source for illuminating at least a portion of said interface, and an opening for light to pass from an interior of said housing to an exterior of said housing for illuminating at least a portion of said interface.

8. An alcohol breath testing device housing in accordance with claim 7 further comprising at least one actuator for controlling illumination of said interface.

9. An alcohol breath testing device housing in accordance with claim 1 further comprising a mouthpiece ejector for facilitating removal of a mouthpiece from said housing.

10. An alcohol breath tester housing assembly for a breath tester comprising:
a housing comprising a base, a display, and a mouthpiece interface, said base being adapted to be gripped by an operator during testing, said base having a front edge and a back edge opposite said front edge, the display disposed on the front edge of the base, said display being disposed on said housing to be in line with an operator's direct line of view while gripping said base;
a mouthpiece configured to be removably coupled to said mouthpiece interface, said mouthpiece comprising an elongate body comprising at least one substantially planar surface, an open end, and a closed end, the closed end and substantially planar surface of the mouthpiece being placed against the mouthpiece interface in a testing position;
said mouthpiece interface being oriented with respect to said base such that when the mouthpiece is coupled thereto, the mouthpiece extends outward from said back edge, and
an alcohol sensor in fluid communication with the mouthpiece and the mouthpiece interface, the alcohol sensor being adapted to detect alcohol present in a subject from a breath sample obtained by the subject blowing into the mouthpiece.

11. An alcohol breath tester housing assembly in accordance with claim 10 wherein said housing further comprises at least one actuator for controlling operation of the breath tester.

12. An alcohol breath tester housing assembly in accordance with claim 11 wherein said at least one actuator comprises a manual sample button located on said back edge of said housing base that is opposite the front edge where said display is located, such that when an operator stands with the subject and said display in the operator's direct field of view, the operator may at any time press said manual sample button without compromising the operator's grip on said base.

13. An alcohol breath tester housing assembly in accordance with claim 10 wherein said housing comprises a first sidewall, an opposite second sidewall coupled to the first sidewall at the front edge and the back edge, said display located on said front edge, said mouthpiece interface located on said top surface.

14. An alcohol breath tester housing assembly in accordance with claim 13 wherein said mouthpiece interface is oriented with respect to said housing such that said mouthpiece extends outward from said back edge of the housing when said mouthpiece is coupled to said mouthpiece interface.

15. An alcohol breath tester housing assembly in accordance with claim 13 wherein said mouthpiece interface is further oriented such that when the mouthpiece is coupled thereto, the mouthpiece extends at least one of obliquely from said top surface and substantially parallel to said top surface.

16. An alcohol breath tester housing assembly in accordance with claim 10 wherein said mouthpiece is further oriented with respect to said housing such that discard breath discharged from said mouthpiece is not directed at the operator.

17. An alcohol breath tester housing assembly in accordance with claim 10 wherein said mouthpiece interface further comprises at least one of a light source for illuminating at least a portion of said interface, and an opening for light to pass from an interior of said housing to an exterior of said housing for illuminating at least a portion of said interface.

18. An alcohol breath tester housing assembly in accordance with claim 17 wherein said housing further comprises at least one actuator for controlling illumination of said interface.

19. An alcohol breath tester housing assembly in accordance with claim 10 wherein said housing further comprises a mouthpiece ejector for facilitating removal of said mouthpiece from said housing.

20. An alcohol breath tester housing assembly in accordance with claim 10 wherein a portion of said mouthpiece has a selected cross-sectional shape, said selected cross-sectional shape being one of: a D-shaped cross-sectional shape and a V-shaped cross-sectional shape.

21. An alcohol breath tester housing assembly in accordance with claim 10 wherein said body further comprising at least one port so that air blown into said body can pass through said port.

22. An alcohol breath tester housing assembly for a breath tester comprising:
a housing comprising a base and a display, said base being configured to be gripped by an operator during testing, said base having a front edge and a back edge opposite said front edge, the display disclosed on the front edge of the base, said display being oriented with respect to said housing to be in line with the operator's direct line of view while gripping said base and while the operator stands in front of a subject in a sideways stance;
a mouthpiece configured to be removably coupled to said housing and to extend obliquely from said housing, said mouthpiece being configured to be pivotally coupled to said housing;
said mouthpiece being oriented with respect to said base such that when the mouthpiece is coupled thereto, the mouthpiece extends outward from said back edge, and
an alcohol sensor in fluid communication with the mouthpiece, the alcohol sensor being adapted to detect alcohol present in the subject by the subject from a breath sample obtained by blowing into the mouthpiece.

23. An alcohol breath tester housing assembly in accordance with claim 22 wherein said housing further comprises a mouthpiece interface sized to receive said mouthpiece in sealing contact therein.

24. An alcohol breath tester housing assembly in accordance with claim 23 wherein said mouthpiece interface comprises at least one of a light source for illuminating at least a portion of said interface, and an opening for light to pass from an interior of said housing to an exterior of said housing for illuminating at least a portion of said interface.

25. An alcohol breath tester housing assembly in accordance with claim 24 wherein said housing further comprises at least one actuator for controlling illumination of said mouthpiece interface.

26. An alcohol breath tester housing assembly in accordance with claim 24 wherein said mouthpiece is further oriented with respect to said housing such that discard breath discharged from said mouthpiece is not directed at the operator.

27. An alcohol breath tester housing assembly in accordance with claim 22 wherein said mouthpiece comprises at least one of a tube and a funnel.

28. An alcohol breath tester housing assembly in accordance with claim 22 wherein said housing comprises at least one actuator for controlling operation of the breath tester, said at least one actuator being located on the back edge of said housing base that is opposite the front edge where said display is located, such that when the operator stands with the subject and said display in the operator's direct field of view, the operator may at any time press said at least one actuator without compromising the operator's grip on said base.

29. An alcohol breath tester housing assembly in accordance with claim 22 wherein said mouthpiece interface being sized and shaped to facilitate positioning said mouthpiece in proper alignment with respect to said housing.

30. An alcohol breath tester housing assembly in accordance with claim 22 wherein said mouthpiece has a selected cross-sectional shape, said selected cross-sectional shape being one of: a D-shaped cross-sectional shape and a V-shaped cross-sectional shape.

31. An alcohol breath tester housing assembly in accordance with claim 22 wherein said mouthpiece comprises a body having a first end and a second end, said first end of said mouthpiece body being closed and the second end of said body being open to enable the subject being tested to blow air into said body, said first end having a semi-circular cross-sectional profile.

32. An alcohol breath testing device comprising:
- a base to be gripped by either hand of an operator and having a front edge and an opposite back edge;
- a display disposed on the front edge and configured for alignment with the operator's direct line of view while gripping the base during use of the breath testing device;
- a removable mouthpiece extending outward from the back edge and away from the display, the mouthpiece including at least one port for channeling air blown into the mouthpiece by a subject into the breath testing device and a discard breath outlet oriented such that discard breath is not directed at the operator of the breath testing device during testing when the operator views the display;
- a mouthpiece interface for receiving the removable mouthpiece, said mouthpiece being configured to pivotally couple with the mouthpiece interface, the mouthpiece interface and mouthpiece being oriented with respect to the base such that, when the operator holds the base in either hand and stands in front of the subject, and the subject blows into the mouthpiece, the display is not in the direct line of view of the subject; and
- an alcohol sensor in fluid communication with the mouthpiece and mouthpiece interface, the alcohol sensor being adapted to detect alcohol present in the subject from a breath sample obtained by the subject blowing into the mouthpiece.

* * * * *